United States Patent
Jang et al.

(10) Patent No.: US 8,273,021 B2
(45) Date of Patent: Sep. 25, 2012

(54) APPARATUS, METHOD AND MEDIUM MEASURING SKIN MOISTURE CONTENT

(75) Inventors: Woo Young Jang, Seoul (KR); Hong Sig Kim, Seongnam-si (KR); Jeong Je Park, Daegu (KR); Sang Ryong Kim, Yongin-si (KR); Kun Soo Shin, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1416 days.

(21) Appl. No.: 11/889,188

(22) Filed: Aug. 9, 2007

(65) Prior Publication Data

US 2008/0045816 A1 Feb. 21, 2008

(30) Foreign Application Priority Data

Aug. 18, 2006 (KR) .................. 10-2006-0078357

(51) Int. Cl.
*A61B 5/00* (2006.01)
*A61B 5/05* (2006.01)
(52) U.S. Cl. .................. 600/307; 600/306; 600/547
(58) Field of Classification Search .................. 600/307, 600/306, 547; 324/60
See application file for complete search history.

(56) References Cited

U.S. PATENT DOCUMENTS

| | | |
|---|---|---|
| 4,013,065 A | 3/1977 | Copeland et al. |
| 4,190,056 A | 2/1980 | Tapper et al. |
| 4,480,921 A | 11/1984 | Leveque et al. |
| 4,483,619 A | 11/1984 | Leveque et al. |
| 4,711,244 A | 12/1987 | Kuzara |
| 4,966,158 A | 10/1990 | Honma et al. |
| 5,353,802 A | 10/1994 | Ollmar et al. |
| 5,738,107 A * | 4/1998 | Martinsen et al. ............. 600/547 |
| 5,795,293 A | 8/1998 | Carim et al. |
| 5,944,661 A | 8/1999 | Swette et al. |
| 6,032,060 A | 2/2000 | Carim et al. |
| 6,119,038 A | 9/2000 | Cook |
| 6,442,422 B1 | 8/2002 | Duckert |
| 6,571,124 B1 * | 5/2003 | Storm ........................... 600/547 |

(Continued)

FOREIGN PATENT DOCUMENTS

JP 6-66619 3/1994

(Continued)

OTHER PUBLICATIONS

Office Action mailed on Apr. 4, 2008 and issued in corresponding Korean Patent Application No. 10-2006-0079524.

(Continued)

*Primary Examiner* — Patricia Mallari
*Assistant Examiner* — Tiffany Weston
(74) *Attorney, Agent, or Firm* — Staas & Halsey LLP

(57) ABSTRACT

An apparatus for measuring skin moisture content in a user's skin is provided. The apparatus may include a signal supplier to generate an out-of-phase signal from a voltage signal obtained from the user's skin and an in-phase signal from the voltage signal, a susceptance measurement unit to measure the susceptance of the voltage signal by synchronizing the voltage signal and the out-of-phase signal received from the signal supplier, a conductance measurement unit to measure the conductance of the voltage signal by synchronizing the voltage signal and the in-phase signal, and an output unit to output sweat gland activity information of the user based on the measured conductance and skin moisture content information of the user based on the measured susceptance.

15 Claims, 6 Drawing Sheets

U.S. PATENT DOCUMENTS

| | | | |
|---|---|---|---|
| 7,753,846 B2 * | 7/2010 | Park et al. | 600/307 |
| 2003/0214311 A1 * | 11/2003 | Alanen et al. | 324/686 |
| 2003/0222662 A1 | 12/2003 | Geisel | |
| 2005/0159655 A1 | 7/2005 | Kao | |
| 2008/0051643 A1 | 2/2008 | Part et al. | |
| 2008/0091091 A1 * | 4/2008 | Jang et al. | 600/306 |
| 2008/0177198 A1 | 7/2008 | Jang et al. | |

FOREIGN PATENT DOCUMENTS

| | | | |
|---|---|---|---|
| JP | 08-056907 | 3/1996 | |
| JP | 9-75316 | 3/1997 | |
| JP | 10-57322 | 3/1998 | |
| JP | 2001-212101 | 8/2001 | |
| JP | 2002-90298 | 3/2002 | |
| JP | 2003-169788 | 6/2003 | |
| JP | 2004-312486 | 11/2004 | |
| JP | 2005-52227 | 3/2005 | |
| WO | WO03/094724 | * 11/2003 | |

OTHER PUBLICATIONS

Extended European Search Report mailed Jan. 21, 2008 and issued in corresponding European Patent Application No. 07114519.7-2319 (in English).

Notice of Allowance dated Apr. 5, 2010 issued in U.S. Patent No. 7,753,846.

Non-Final Office Action dated Oct. 29, 2009 issued in U.S. Patent No. 7,753,846.

* cited by examiner

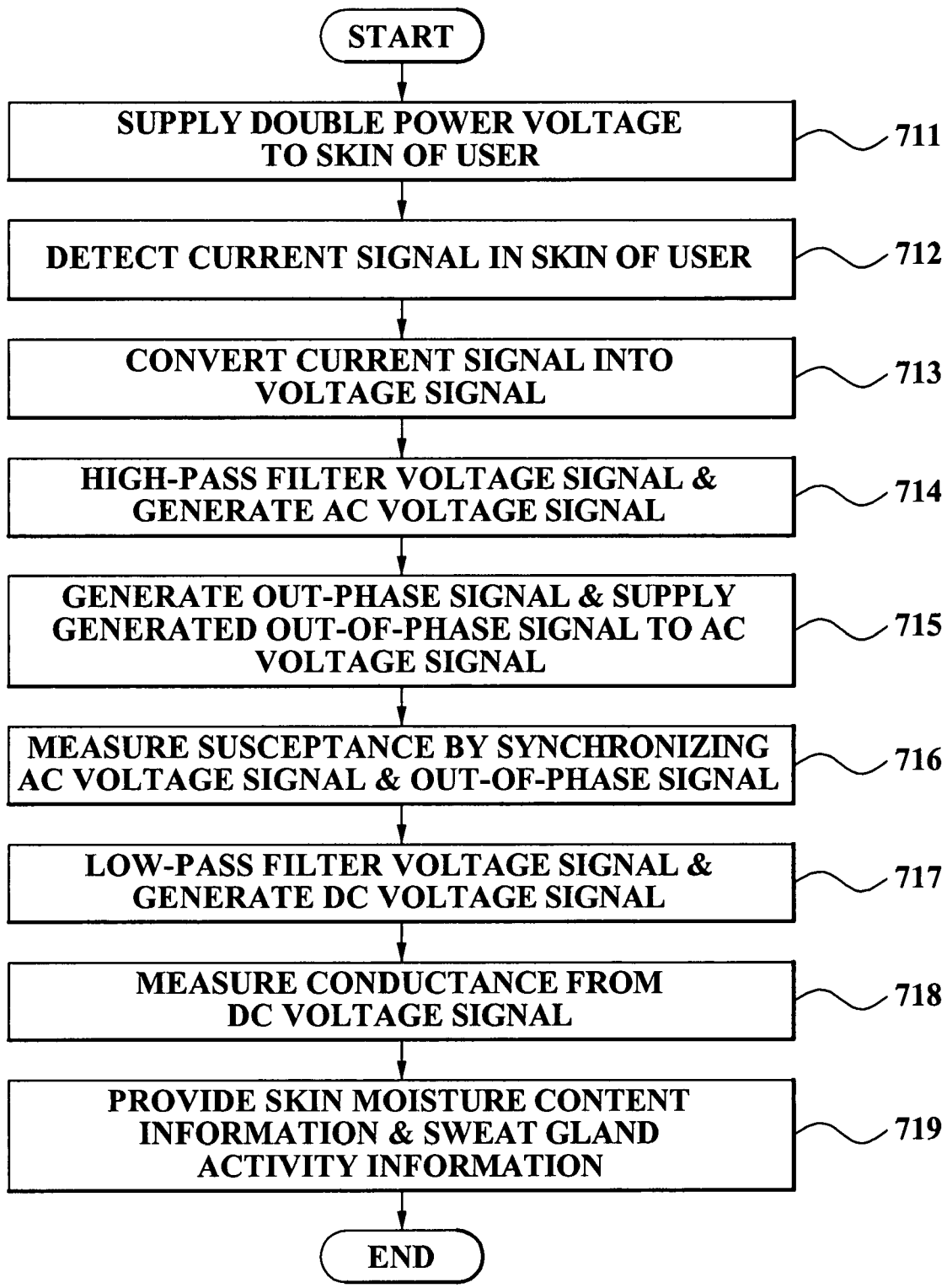

APPARATUS, METHOD AND MEDIUM MEASURING SKIN MOISTURE CONTENT

CROSS-REFERENCE TO RELATED APPLICATIONS

This application claims the benefit of Korean Patent Application No. 10-2006-0078357, filed on Aug. 18, 2006, in the Korean Intellectual Property Office, the disclosure of which is incorporated herein by reference.

BACKGROUND

1. Field

One or more embodiments of the present invention relate to an apparatus, method and medium measuring skin moisture content, and more particularly, to an apparatus, method and medium measuring skin moisture content, which can more accurately measure skin moisture content by measuring sweat gland activity when measuring the skin moisture content in a stratum corneum of the skin of a user, and thereby taking into account the effect of the sweat gland activity on the skin moisture content, due to stress, for example.

2. Description of the Related Art

As people become more interested in beauty, interest in skin care has also increased. Market demand for products promoting healthy skin affects not only beauty-related businesses, but also affects the growth of medical-related businesses since people need to protect their skin from ultraviolet rays that have become stronger due to the destruction of the ozone layer, and various types of pollutions.

The skin is an organ of the integumentary system made up of multiple layers of epithelial tissues. The main functions of skin include protecting against pathogens, waterproofing, temperature regulation, insulation, and the like. One of the most critical elements to enable the proper performance of the functions of skin is moisture content in a stratum corneum. The moisture content in the stratum corneum is generally called skin moisture content. When maintaining a minimum moisture content in the stratum corneum, to skin is able to perform its basic functions such as protecting against harmful substances like pathogens, and preventing excessive evaporation of skin moisture.

In view of skin care, skin moisture content is considered an essential element. Accordingly, skin moisture management is fundamental to skin care.

According to a conventional art, an electrical measurement technique, an optical measurement technique, and a technique using a magnetic resonance imaging (MRI) are used for measuring skin moisture content. The electrical measurement technique is widely used. More specifically, a method of measuring skin moisture content by measuring susceptance, i.e. an alternating current (AC) component of admittance, of three electrodes using a sinusoidal wave of low frequency is generally used.

Also, sweat gland activity of the skin may be measured via a galvanic skin response (GSR) or an electrodermal response (EDR). The sweat gland activity of the skin may be used to measure a sensibility status or stress of a human body. Generally, sweat gland activity may be measured via a direct current (DC) voltage. Also, a technique of measuring the sweat gland activity via an alternating current (AC) voltage to remove an effect of a contact resistance is currently in use.

As described above, skin moisture content refers to moisture content in only a stratum corneum. Thus, the accurate measurement of the moisture content in the stratum corneum is most important when measuring skin moisture content. Epidermis and corium of skin, excluding the stratum corneum, contain enough moisture at all times. Thus, so that the skin appropriately protects against external environments, it is important that sufficient moisture is contained in the stratum corneum made up of dead cells, for example, Keratin, lipid, and the like.

Although each skin portion has a different density, sweat glands corresponding to sweat paths exist in the stratum corneum. Since the sweat glands contain a great amount of moisture, the sweat glands may affect measurement of skin moisture content. Specifically, the skin moisture content designates a moisture content in the stratum corneum, and sweat glands also exists in the same anatomical area where the skin moisture content is measured. Thus, when sweat gland activity affects the measurement, an error may occur.

As described above, when measuring the skin moisture content, i.e. even when measuring the skin moisture content in any anatomical area of the skin, the most important factor may be to reduce an effect of the sweat glands and thereby measure moisture content in only the stratum corneum. Thus, a method of measuring skin moisture content, which can reduce an effect of the sweat glands and accurately measure skin moisture content in only a stratum corneum when measuring the skin moisture content, and thereby can provide a user with skin moisture content information taking sweat gland activity into account, is required.

SUMMARY

One or more embodiments of the present invention relate to an apparatus, method and medium measuring skin moisture content, which can simultaneously measure skin moisture content and a sweat gland activity in a stratum corneum when measuring the skin moisture content, and provide a user with skin moisture content information including the sweat gland activity.

One or more embodiments of the present invention also relate to an apparatus, method and medium measuring skin moisture content, which can determine a user's stress via a measured sweat gland activity and provide the user with stress information and skin moisture content information including the sweat gland activity.

Additional aspects and/or advantages will be set forth in part in the description which follows and, in part, will be apparent from the description, or may be learned by practice of the invention.

To achieve at least the above and/or other aspects and advantages, embodiments of the present invention include an apparatus measuring skin moisture content, the apparatus including, an electrode module to supply a predetermined voltage to skin of a user and detecting a current signal in the skin of the user, and a measurement control module to measure the skin moisture content and a sweat gland activity of the user using the current signal and a predetermined phase signal generated with respect to the current signal.

To achieve at least the above and/or other aspects and advantages, embodiments of the present invention include an apparatus for measuring skin moisture content, the apparatus including, an electrode module to supply a predetermined voltage to a user's skin, and detecting a current signal in the user's skin, and a measurement control module to measure the skin moisture content and a sweat gland activity of the user using a direct current (DC) signal and an alternating current (AC) signal of the current signal.

To achieve at least the above and/or other aspects and advantages, embodiments of the present invention include a method of measuring skin moisture content, the method including, generating an in-phase signal and an out-of-phase signal based on a voltage signal obtained from a user's skin, and supplying the generated in-phase signal and the out-of-phase signal to the voltage signal, measuring conductance of the voltage signal by synchronizing the voltage signal and the in-phase signal, and measuring susceptance of the voltage signal by synchronizing the voltage signal and the out-of-phase signal.

To achieve at least the above and/or other aspects and advantages, embodiments of the present invention include a method of measuring skin moisture content, the method including, supplying a single power voltage to the skin of a user, and detecting a current signal in the skin of the user, converting the current signal into a voltage signal, high-pass filtering the voltage signal to generate an AC voltage signal, generating an out-of-phase signal with respect to the voltage signal to supply to the AC voltage signal, measuring susceptance of the current signal by synchronizing the AC voltage signal and the out-of-phase signal, low-pass filtering the voltage signal to generate a DC voltage signal, and measuring conductance of the current signal from the DC voltage signal.

To achieve at least the above and/or other aspects and advantages, embodiments of the present invention include an apparatus measuring skin moisture content in a user's skin, the apparatus including, a signal supplier to generate an out-of-phase signal from a voltage signal obtained from the user's skin and an in-phase signal from the voltage signal, a susceptance measurement unit to measure the susceptance of the voltage signal by synchronizing the voltage signal and the out-of-phase signal received from the signal supplier, a conductance measurement unit to measure the conductance of the voltage signal by synchronizing the voltage signal and the in-phase signal, and an output unit to output sweat gland activity information of the user based on the measured conductance and skin moisture content information of the user based on the measured susceptance.

BRIEF DESCRIPTION OF THE DRAWINGS

These and/or other aspects and advantages will become apparent and more readily appreciated from the following description of the embodiments, taken in conjunction with the accompanying drawings of which:

FIG. 7 illustrates a method measuring skin moisture content according to an embodiment of the present invention.

DETAILED DESCRIPTION OF EMBODIMENTS

Figure 1:
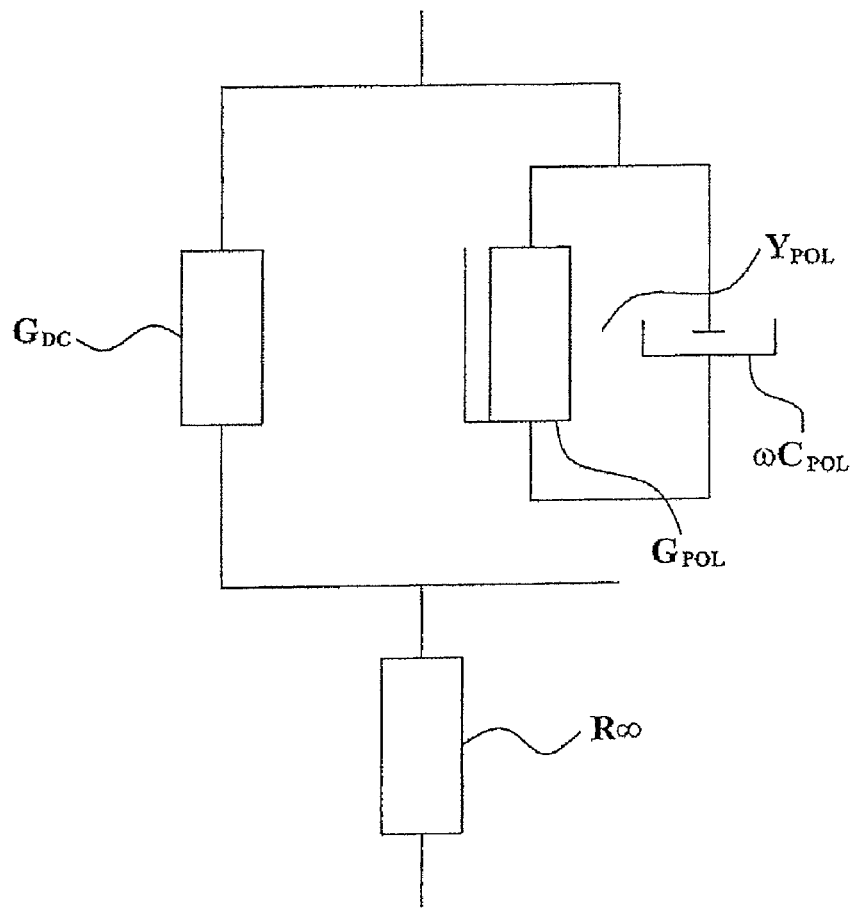
FIG. 1 illustrates an electrically modeled biological structure of skin.

Reference will now be made in detail to the embodiments, examples of which are illustrated in the accompanying drawings, wherein like reference numerals refer to the like elements throughout. The embodiments are described below to explain the present invention by referring to the figures.

An apparatus for measuring skin moisture content according to embodiments of the present invention may be embodied as any portable device including, for example, a mobile communication terminal, a personal digital assistance (PDA), a portable game device, an Moving Picture Experts Group Audio-Layer 3 (MP3) player, a portable multimedia player (PMP), a Digital Multimedia Broadcasting (DMB) terminal, and a notebook computer. More specifically, the apparatus for measuring skin moisture content may be embodied as a partial configuration of the portable device or may alternatively be independently embodied as a stand-alone device.

The apparatus for measuring skin moisture content according to embodiments of the present invention may measure each of skin moisture content and a sweat gland activity by electrically modeling a biological structure of skin. Hereinafter, a measurement principle for measuring skin moisture content and sweat gland activity, according to electrical modeling of the skin, will be described with reference to FIGS. 1 through 3. Also, an apparatus, method and medium measuring skin moisture content, according to embodiments of the present invention will be described with reference to FIGS. 4 through 7.

To electrically measure skin moisture content, it is required to electrically model the biological structure of the skin. FIG. 1 illustrates an electrically modeled biological structure of skin by using a Yamamoto-Yamamoto model, *The measurement principle for evaluating the performance of drugs and cosmetics by skin impedance* in Med. & Biol. Eng. & Comput. 1978. The Yamamoto-Yamamoto model reinterpreted a Cole-Cole model, *Dispersion and absorption in dielectrics*, in J. Soc. Cosmet. Chem. 1941.

In FIG. 1, $G_{DC}$ generally indicates a sweat gland activity of a stratum corneum. $R_\infty$ indicates a value which is acquired by electrically modeling a liable cell from a bottom of a stratum corneum to a dermis. The $R_\infty$ is direct current (DC) dominant, $Y_{POL}$ indicates an admittance component due to a polarizing phenomenon, and is alternating current (AC) dominant. A $\omega C_{POL}$ component is known to model the skin moisture content of the stratum corneum. Accordingly, when measuring the skin moisture content of the stratum corneum, removing an effect of the $R_\infty$ and the $G_{DC}$ may become important.

To measure only the $\omega C_{POL}$ component, only susceptance, which is an AC component of the admittance component, may be required to be measured. For this, an analog lock-in amplifier may be utilized.

Figure 2:
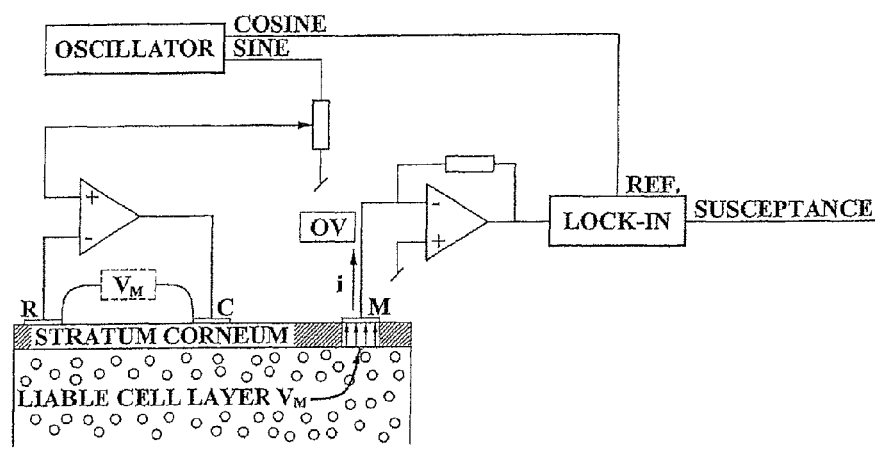
FIG. 2 illustrates a measurement principle of measuring skin moisture content.

Specifically, the $R_\infty$ may be assumed to be a conductor as shown in FIG. 2. When a constant voltage signal of a regular frequency, for example, $\omega=2\pi f$, is supplied to a human body using $R_\infty$ as the conductor, a current, which reacts to an impedance of the stratum corneum, may be measured through the conductor of a liable cell layer. In this instance, the stratum corneum closely attaches to a measurement electrode. The admittance of the stratum corneum of a measured area may be measured using the current.

A response signal which converts the measured current to a voltage may be represented, for example, as in Equation 1 below.

$$V_{sig} = |V_{sig}|\sin(\omega rt + \theta_{sig}) \qquad \text{Equation 1}$$

Also, an out-of-phase reference signal having a phase difference of 90° to be synchronous with the response signal may be represented, for example, as in Equation 2 below.

$$V_{L\_90} = |V_{L\_90}|\cos(\omega_{L\_90}t + \theta_{ref\_90}) \qquad \text{Equation 2}$$

Here, an in-phase reference signal having a phase difference of 0° to be synchronous with the response signal may be represented, for example, as in Equation 3 below.

$$V_{L\_O} = |V_{L\_0}|\sin(\omega_{L\_0}t + \theta_{ref\_0}) \qquad \text{Equation 3}$$

In this instance, when synchronizing the response signal and the reference signal having the phase difference of 90° using a multiplier, a signal may be generated by, for example, Equation 4 below.

$$V_{PSD} = |Vsig||V_{L\_90}|\sin(\omega rt + \theta sig)\cos(\omega L\_90 t + \theta_{ref\_90}) =$$
$$1/2|Vsig||V_{L\_90}|\{\sin([\omega r - \omega_{L\_90}]t + \theta sig - \theta_{ref\_90}) -$$
$$\sin([\omega r + \omega_{L\_90}]t + \theta sig + \theta_{ref\_90})\}$$

Equation 4

Also, when the signal passes through a low-pass filter (LPF), the AC component may be removed from the signal. Accordingly, $V_{PSD}$ may become "0".

However, when frequencies of the reference signal and the response signal are identical, i.e. $\omega r = \omega_{L\_90}$, an output of the LPF may be represented, for example, as in Equation 5 below.

$$Vout\_90 = \frac{1}{2}|Vsig||V_{L\_90}|\sin(\theta sig - \theta_{ref\_90})$$

Equation 5

Also, when synchronizing the in-phase reference signal and the response signal by a method as described above, it may be given, for example, by Equation 6 below.

$$Vout\_0 = \frac{1}{2}|Vsig||V_{L\_0}|\cos(\theta sig - \theta_{ref\_0})$$

Equation 6

Also, when $|VSig||V_L|$=Vout and $\theta si - \theta ref = \theta out$ to simplify the equations with respect to the Vout_90 and Vout_0, it may be arranged by, for example, Equation 7 below.

$$V_{PSD\_filtered\_0} = \frac{1}{2}Vout\cos(\theta out)$$

Equation 7

Figure 3:
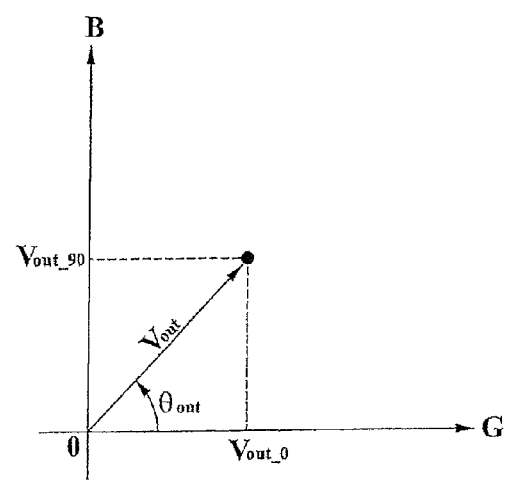
FIG. 3 illustrates a graph of an admittance by a skin moisture content measurement result.

The equations with respect to the Vout_90 and Vout_0, i.e. Equation 5 and Equation 6 designate a conductivity signal which may be generated by supplying a constant AC voltage, and measuring the current. Accordingly, the admittance may be measured. FIG. 3 illustrates a graph of the admittance. In FIG. 3, G designates conductance, and B designates susceptance. When G and an in-phase synchronous signal are combined, G may be measured. When B and a quadrature-phase synchronous signal are combined, B may be measured.

As described above, the skin moisture content may be measured from susceptance measured via an out-of-phase signal. Also, the sweat gland activity may be measured from conductance measured via an in-phase signal.

A method of measuring skin moisture content by measuring susceptance and a method of measuring sweat gland activity of skin by measuring conductance have been described with reference to FIGS. 1 through 3, and may be applied as a structure and operation principle of an apparatus measuring skin moisture content, according to embodiments of the present invention, which will be described in greater detail with reference to FIGS. 4 through 7.

According to embodiments of the present invention, there is provided a method, medium and apparatus measuring skin moisture content, which can simultaneously measure a user's skin moisture content and sweat gland activity by simultaneously measuring susceptance and conductance as described above. Here, the apparatus for measuring skin moisture content, according to embodiments of the present invention, may include various embodiments based on the principles of susceptance and conductance measurement described herein.

Hereinafter, a structure and operation of an apparatus for measuring skin moisture content according to an embodiment of the present invention will be described with reference to FIG. 4. Also, a structure and operation of an apparatus for measuring skin moisture content according to another embodiment of the present invention will be described with reference to FIG. 5.

Figure 4:
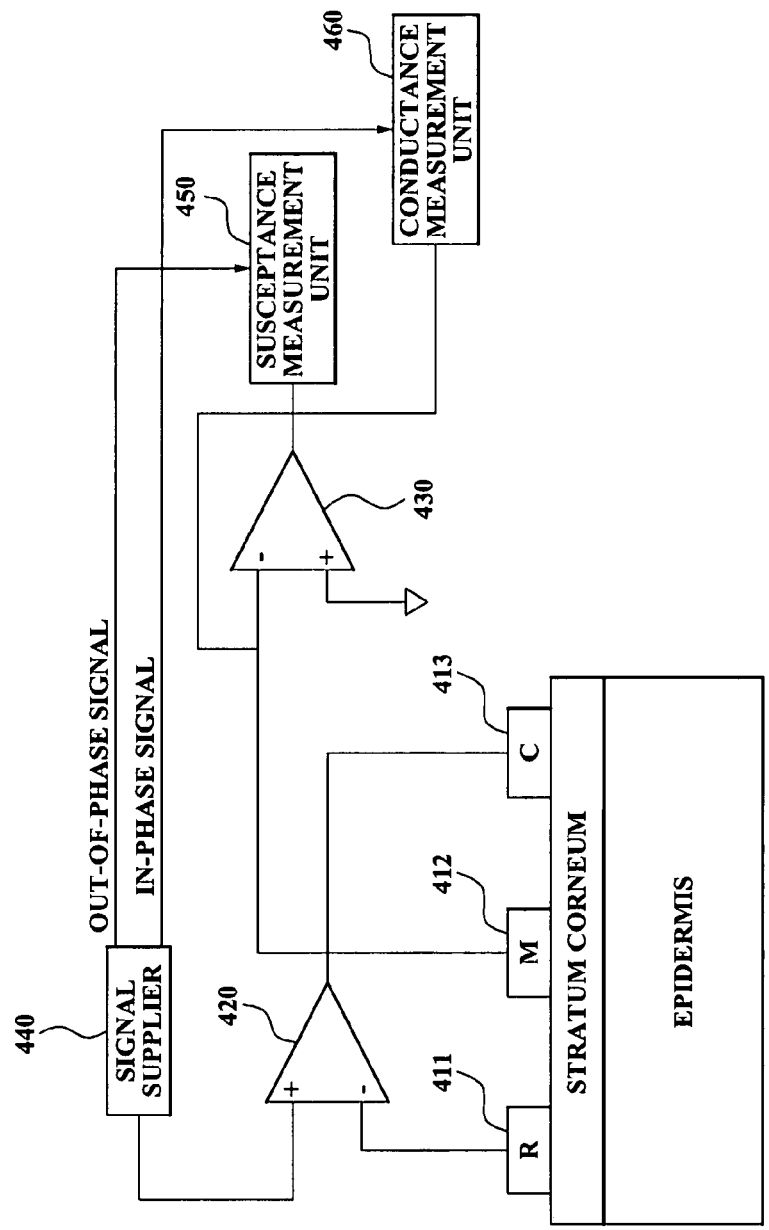
FIG. 4 illustrates an apparatus measuring skin moisture content, according to an embodiment of the present invention.

FIG. 4 illustrates an apparatus measuring skin moisture content, according to an embodiment of the present invention.

The apparatus measuring skin moisture content, according to an embodiment may include, an electrode module and a measurement control module. The electrode module may include at least one electrode unit and a voltage supplier 420. Also, the measurement control module may include, for example, a signal converter 430, a signal supplier 440, a susceptance measurement unit 450, and a conductance measurement unit 460.

The electrode unit may include, for example, a reference (R) electrode 411, a measuring (M) electrode 412, and a current (C) electrode 413. Specifically, as well-known to those of ordinary skill in the art, the electrode unit may be constructed to include the R electrode 411, the M electrode 412, and the C electrode 413. Also, the electrode unit may be constructed to include any type of electrode that can measure the skin moisture content.

The voltage supplier 420 may supply two power voltages to the electrode unit. Here, a voltage value of the two power voltages may be set to various values depending upon the circumstances. The two power voltages may be supplied to the skin of a user via the R electrode 411 and the C electrode 413. When the voltage supplied to the skin is influenced by an impedance of a stratum corneum, a predetermined current signal may be generated. The M electrode 412 typically detects the generated current signal and transmits the detected current signal to the signal converter 430.

The signal converter 430 may convert the detected current signal into a voltage signal. Here, the signal converter 430 may include, for example, an operational amplifier to convert the current signal into the voltage signal.

The signal supplier 440 may generate an in-phase signal and an out-of-phase signal with respect to the voltage signal, and supply the generated in-phase signal and the out-of-phase signal to the voltage signal. Specifically, the signal supplier 440 may generate the out-of-phase signal required to measure susceptance from the voltage signal, and transmit the generated out-of-phase signal to the susceptance measurement unit 450. Here, the out-of-phase signal may have a phase difference of 90° with respect to the voltage signal, and may be embodied as a cosine wave.

Also, the signal supplier 440 may generate the in-phase signal required to measure conductance from the voltage signal, and transmit the generated in-phase signal to the conductance measurement unit 460. Here, the in-phase signal may have a phase difference of 0° with respect to the voltage signal, and may be embodied as a sine wave. Also, the signal supplier 440 may include, for example, an oscillator to generate and supply the out-of-phase signal and the in-phase signal.

The susceptance measurement unit 450 may receive the voltage signal from the signal converter 430, and the out-of-phase signal from the signal supplier 440. Also, the susceptance measurement unit 450 may synchronize the voltage signal and the out-of-phase signal and measure the susceptance of the current signal. Also, the susceptance measurement unit 450 may synchronize the voltage signal and the out-of-phase signal using a multiplier.

As an example, as described above with reference to FIGS. 1 through 3, the voltage signal may be represented as:

$$Vsig = |Vsig|\sin(\omega rt + \theta sig).$$

Also, the out-of-phase signal may be represented as:

$$V_{L\_90} = |V_{L\_90}|\cos(\omega_{L\_90}t + \theta_{ref\_90}).$$

By synchronizing the voltage signal and the out-of-phase signal, the susceptance measurement unit 450 may output, for example:

$$V\text{out\_90} = \tfrac{1}{2}|Vsig||V_{L\_90}|\sin(\theta sig - \theta_{ref\_90}).$$

Here, since the signal designates a conductivity signal generated by supplying a constant AC voltage and measuring the current, the admittance may be measured. When representing the signal into a rectangular form, it may be illustrated as in the graph of FIG. 3.

In FIG. 3, the graph may be represented as $Y=G+iB$ where Y designates the admittance, G designates the conductance, and B designates the susceptance. Here, when B is synchronized with the out-of-phase signal, B may be measured. Specifically, the susceptance measurement unit 450 may measure the susceptance of the current signal by synchronizing the voltage signal and the out-of-phase signal. Also, the susceptance measurement unit 450 may output the user's skin moisture content information using the measured susceptance.

The susceptance measurement unit 450 may be embodied as a lock-in amplifier with a predetermined multiplier to synchronize the voltage signal and the out-of-phase signal as described above.

The conductance measurement unit 460 may receive the voltage signal from the signal converter 430 and the in-phase signal from the signal supplier 440. Also, the conductance measurement unit 460 may synchronize the voltage signal and the in-phase signal and measure the conductance of the current signal. Also, the conductance measurement unit 460 may synchronize the voltage signal and the in-phase signal using, e.g., a multiplier.

As an example, as described above with FIGS. 1 through 3, the voltage signal may be represented as:

$$Vsig = |Vsig|\sin(\omega wrt + \theta sig).$$

Also, the in-phase signal may be represented as:

$$V_{L\_0} = |V_{L\_0}|\sin(\omega_{L\_0}t + \theta_{ref\_0}).$$

By synchronizing the voltage signal and the in-phase signal, the conductance measurement unit 460 may output:

$$V\text{out\_0} = \tfrac{1}{2}|Vsig||V_{L\_0}|\cos(\theta sig - \theta_{ref\_0}).$$

Here, since the signal designates a conductivity signal generated by supplying the constant AC voltage and measuring the current, the admittance may be measured. When representing the signal in a rectangular form, it may be illustrated as the graph of FIG. 3.

As described above, the graph of FIG. 3 may be represented as $Y=G+iB$. Here, when C is synchronized with the in-phase signal, C may be measured. Specifically, the conductance measurement unit 460 may measure the conductance of the current signal by synchronizing the voltage signal and the in-phase signal. Also, the conductance measurement unit 460 may output the user's sweat gland activity information using the measured conductance.

The conductance measurement unit 460 may be embodied in a lock-in amplifier with a predetermined multiplier to synchronize the voltage signal and the in-phase signal as described above.

As described above with reference to FIG. 4, the apparatus measuring skin moisture content according to an embodiment of the present invention may simultaneously measure the user's skin moisture content and sweat gland activity by measuring the susceptance and the conductance of the current signal that is detected from the user skin, supplied by the two power voltages, via the M electrode 412. To measure the susceptance and the conductance, the apparatus measuring skin moisture content according to an embodiment may include at least two lock-in amplifiers with a predetermined multiplier.

Hereinafter, a structure and operation of an apparatus measuring skin moisture content when supplying a single power voltage to the skin of a user according to an embodiment of the present invention will be described with reference to FIG. 5.

Figure 5:
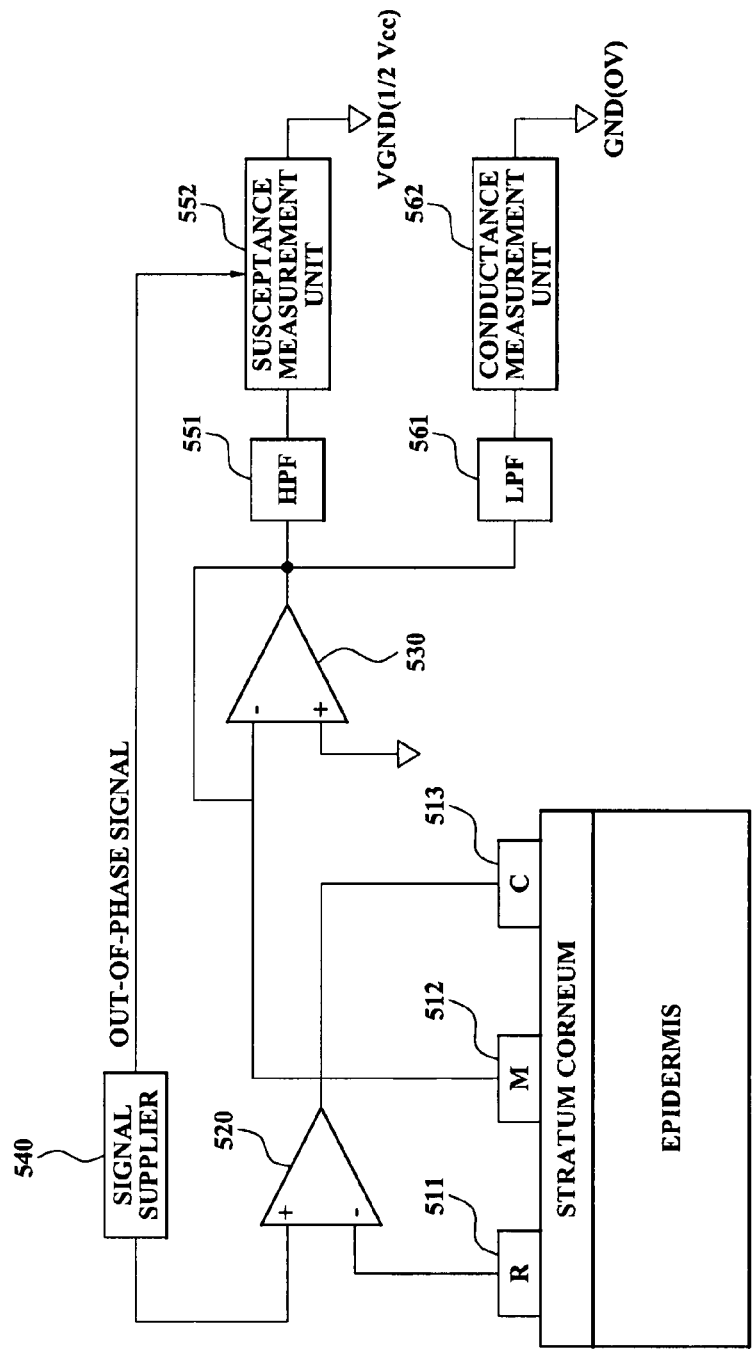
FIG. 5 illustrates an apparatus measuring skin moisture content according to an embodiment of the present invention.

FIG. 5 illustrates an apparatus measuring skin moisture content, according to an embodiment of the present invention.

The apparatus measuring skin moisture content, according to an embodiment may include an electrode module and a measurement control module. The electrode module may include at least one electrode unit and a voltage supplier 520. Also, the measurement control module may include, for example, a signal converter 530, a signal supplier 540, a high-pass filter (HPF) 551, a susceptance measurement unit 552, a low-pass filter 561, and a conductance measurement unit 562.

The electrode unit may include an R electrode 511, an M electrode 512, and a C electrode 513. Specifically, as well-known to those of ordinary skill in the art, the electrode unit may be constructed to include the R electrode 511, the M electrode 512, and the C electrode 513. Also, the electrode unit may be constructed to include any type of electrode that can measure the skin moisture content.

The voltage supplier 520 may supply a single power voltage to the electrode unit. Here, a voltage value of the single power voltage may be set to various values depending upon the circumstances. The single power voltage may be supplied to the skin of a user via the R electrode 511 and the C electrode 513. When the voltage supplied to the skin reacts with an impedance of a stratum corneum, a predetermined current signal may be generated. The M electrode 512 may detect the generated current signal, and transmit the detected current signal to the signal converter 530.

The signal converter 530 may convert the detected current signal into a voltage signal. Here, the converted voltage signal may include an AC component and a DC component since the voltage supplied to the user skin by the voltage supplier 520 corresponds to a single power voltage.

Specifically, when the single power voltage is $V_{cc}$, $\tfrac{1}{2} V_{cc}$ may be utilized as a virtual ground (VGND). Accordingly, the voltage signal that is converted by the signal converter 530 may include both the AC component and the DC component at the same time. The signal converter 530 may include an operational amplifier to convert the current signal into the voltage signal.

The HPF 551 high-pass filters the voltage signal, which is received from the signal converter 530, and may generate an AC voltage signal. Specifically, the HPF 551 may generate the AC voltage signal by extracting only the AC component from the voltage signal and not the DC component of the voltage signal.

The signal supplier 540 may generate an out-of-phase signal with respect to the AC voltage signal and supply the generated out-of-phase signal to the AC voltage signal. Specifically, the signal supplier 540 may generate the out-of-phase signal required to measure susceptance from the AC voltage signal and transmit the generated out-of-phase signal to the susceptance measurement unit 552. Here, the out-of-phase signal may have a phase difference of 90° with the AC voltage signal, and may be embodied as a cosine wave. Also, the signal supplier 540 may include an oscillator to generate and supply the out-of-phase signal.

The susceptance measurement unit 552 may synchronize the AC voltage signal and the out-of-phase signal and measure the susceptance of the current signal. The susceptance measurement unit 552 may synchronize the AC voltage signal and the out-of-phase signal using a multiplier.

As an example, as described with FIGS. 1 through 3, the AC voltage signal may be represented as:

$$V_{sig} = |V_{sig}| \sin(\omega_{rt} + \theta_{sig}).$$

Also, the out-of-phase signal may be represented as:

$$V_{L\_90} = |V_{L\_90}| \cos(\omega_{L\_90} t + \theta_{ref\_90}).$$

By synchronizing the AC voltage signal and the out-of-phase signal, the susceptance measurement unit 552 may output:

$$V_{out\_90} = \tfrac{1}{2} |V_{sig}| |V_{L\_90}| \sin(\theta_{sig} - \theta_{ref\_90}).$$

Here, since the signal designates a conductivity signal generated by supplying a constant AC voltage and measuring the current, the admittance may be measured. When representing the signal in a rectangular form, it may be illustrated as the graph of FIG. 3.

In FIG. 3, the graph may be represented as $Y = G + iB$ where Y designates the admittance, G designates the conductance, and B designates the susceptance. Here, when B is synchronized with the out-of-phase signal, B may be measured. Specifically, the susceptance measurement unit 552 may measure the susceptance of the current signal by synchronizing the AC voltage signal and the out-of-phase signal. Also, the susceptance measurement unit 552 may output the user's skin moisture content information by using the measured susceptance.

The susceptance measurement unit 450 may be embodied in a lock-in amplifier with a predetermined multiplier to synchronize the AC voltage signal and the out-of-phase signal as described above.

The LPF 561 low-pass filters the voltage signal received from the signal converter 530 and may generate a DC voltage signal. Specifically, the LPF 561 may generate the DC voltage signal by extracting only the DC component of the voltage signal, and not the AC component of the voltage signal.

The conductance measurement unit 562 may measure conductance of the current signal from the DC voltage signal. Specifically, as described above, a galvanic skin response (GSR) used to measure sweat gland activity, usually reacts when a DC signal is supplied. Descriptions related thereto have been made with reference to FIG. 1, a circuit diagram illustrating an electrically modeled biological structure of skin. Accordingly, the conductance measurement unit 562 may measure the conductance of the DC voltage signal and measure the sweat gland activity of the skin of the user from the measured conductance.

The conductance measurement unit 562 may be constructed as a predetermined signal processing module to measure the conductance and also measure the sweat gland activity according to the measured conductance. Specifically, according to an embodiment of the present invention, the conductance measurement unit 562 may not include the lock-in amplifier with a multiplier, but may be configured into a software module that records a program for measuring the conductance and the sweat gland activity.

As described above with reference to FIG. 5, the apparatus measuring skin moisture content according to an embodiment of the present invention may supply a single power voltage to the skin of the user and then convert a detected current signal into a voltage signal. Also, the apparatus for measuring the skin moisture content may output the user's skin moisture content information from the AC component of the voltage signal and the user's sweat gland activity information from the DC component of the voltage signal.

Figure 6:
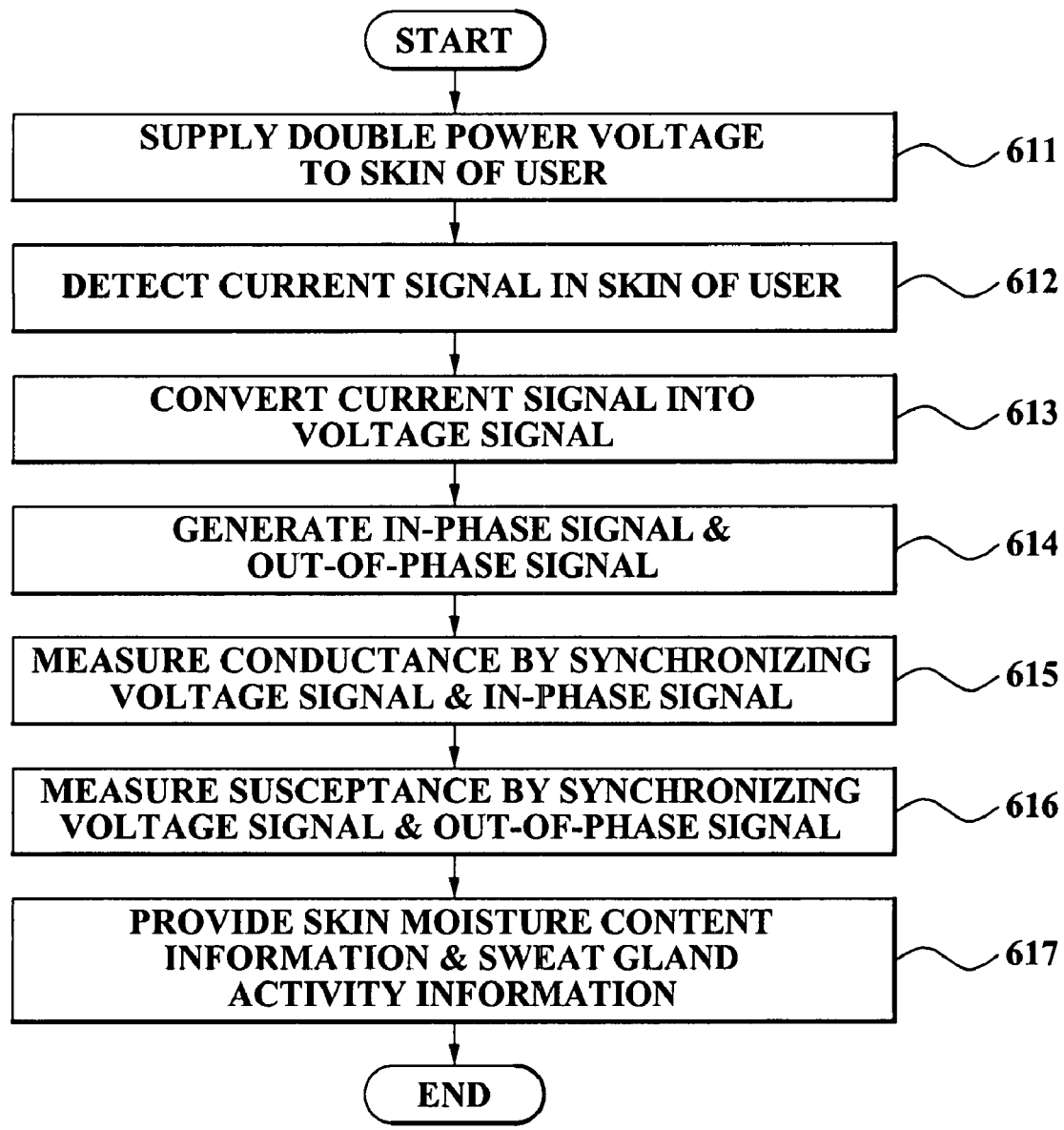
FIG. 6 illustrates a method measuring skin moisture content according to an embodiment of the present invention.

FIG. 6 illustrates a method measuring skin moisture content, according to an embodiment of the present invention.

In operation 611, an apparatus measuring skin moisture content, according to an embodiment of the present invention, may supply two power voltages to the skin of a user to measure the user's skin moisture content information and sweat gland activity information. In operation 612, the apparatus may detect a current signal in the skin of the user according to the supply of the two power voltages. In operation 613, the apparatus may convert the current signal into a voltage signal.

In operation 614, the apparatus may generate an in-phase signal and an out-of-phase signal with respect to the voltage signal and supply the generated in-phase signal and the out-of-phase signal to the voltage signal.

In operation 615, the apparatus may measure conductance of the current signal by synchronizing the voltage signal and the in-phase signal. In operation 616, the apparatus may measure susceptance of the current signal by synchronizing the voltage signal and the out-of-phase signal.

In operation 617, the apparatus may output the user's sweat gland activity information from the measured conductance and the user's skin moisture content information from the measured susceptance, and provide the user with the outputted information, e.g. using a display (not shown).

FIG. 7 illustrates a method measuring skin moisture content, according to an embodiment of the present invention.

In operation 711, the apparatus measuring skin moisture content according to an embodiment of the present invention may supply a single power voltage to the skin of a user to measure the user's skin moisture content information and sweat gland activity information. In operation 712, the apparatus may detect a current signal in the skin of the user according to supply of the single power voltage. In operation 713, the apparatus may convert the current signal into a voltage signal.

In operation 714, the apparatus high-pass filters the voltage signal and may generate an AC voltage signal. In operation 715, the apparatus may generate an out-of-phase signal with respect to the voltage signal, and supply the generated out-of-phase signal to the AC voltage signal. In operation 716, the apparatus may measure susceptance of the current signal by synchronizing the AC voltage signal and the out-of-phase signal.

In operation 717, the apparatus low-pass filters the voltage signal and may generate a DC voltage signal. In operation 718, the apparatus may measure conductance of the current signal from the DC voltage signal.

In operation 719, the apparatus may output the user's sweat gland activity information from the measured conductance and the user's skin moisture content information from the measured susceptance, and provide the user with the outputted information.

Methods measuring skin moisture content according to embodiments of the present invention have been described with reference to FIGS. 6 and 7. The methods measuring skin moisture content may utilize a configuration and operation of the apparatus measuring skin moisture content according to embodiments of the present invention, which have been described herein with respect to FIGS. 1 through 5, or may equally include other configurations not previously described herein, noting that the described system and method are mutually exclusive and should not be limited to the same.

In addition to the above described embodiments, embodiments of the present invention may also be implemented through computer readable code/instructions in/on a medium, e.g., a computer readable medium, to control at least one processing element to implement any above described embodiment. The medium can correspond to any medium/media permitting the storing and/or transmission of the computer readable code.

The computer readable code may be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as carrier waves, as well as through the Internet, for example. Thus, the medium may further be a signal, such as a resultant signal or bitstream, according to embodiments of the present invention. The media may also be a distributed network, so that the computer readable code is stored/transferred and executed in a distributed fashion. Still further, as only an example, the processing element could include a processor or a computer processor, and processing elements may be distributed and/or included in a single device.

According to the above-described embodiments of the present invention, an apparatus, method and medium measuring skin moisture content can simultaneously measure skin moisture content and sweat gland activity in a stratum corneum when measuring the skin moisture content, and can provide a user with skin moisture content information taking the sweat gland activity into consideration.

According to the above-described embodiments of the present invention, an apparatus, method and medium measuring skin moisture content can determine a user's stress via a measured sweat gland activity and provide the user with stress information and skin moisture content information taking the sweat gland activity into consideration.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. An apparatus measuring skin moisture content, the apparatus comprising:
   an electrode module to supply a predetermined voltage to a skin of a user and detecting a current signal in the skin of the user; and
   a measurement control module to measure the skin moisture content and a sweat gland activity of the user using the current signal and a predetermined phase signal generated with respect to the current signal, wherein the measurement control module comprises:
   a susceptance measurement unit to measure susceptance of a voltage signal by synchronizing the voltage signal and an out-of-phase signal generated from the voltage signal;
   a conductance measurement unit to measure conductance of the voltage signal by synchronizing the voltage signal and an in-phase signal generated from the voltage signal, wherein the conductance measurement unit measures the conductance simultaneously with the susceptance measurement unit's measurement of the susceptance; and
   an output unit to simultaneously output sweat gland activity information of the user based on the measured conductance and skin moisture content information of the user based on the measured susceptance, thereby providing skin moisture content information that takes sweat gland activity into account.

2. The apparatus of claim 1, wherein the electrode module comprises:
   at least one electrode unit comprising a reference (R) electrode, a current (C) electrode, and a measuring (M) electrode; and
   a voltage supplier to supply two power voltages to the electrode unit.

3. The apparatus of claim 2, wherein the electrode unit supplies the voltage to the skin of the user via the R electrode and the C electrode, and detects the current signal via the M electrode, and the current signal is generated by the voltage and an impedance of a stratum corneum of the skin of the user.

4. An apparatus measuring skin moisture content, the apparatus comprising:
   an electrode module to supply a predetermined voltage to a user's skin, and detecting a current signal in the user's skin;
   a measurement control module to measure the skin moisture content and a sweat gland activity of the user using a direct current (DC) signal and an alternating current (AC) signal of the current signal; and
   an output unit to simultaneously output the sweat gland activity information and the skin moisture content information of the user thereby providing skin moisture content information that takes sweat gland activity into account.

5. The apparatus of claim 4, wherein the electrode module comprises:
   at least one electrode unit comprising an R electrode, a C electrode, and an M electrode; and
   a voltage supplier to supply a single power voltage to the electrode unit.

6. The apparatus of claim 5, wherein the electrode unit supplies the voltage to the user's skin via the R electrode and the C electrode, and detects the current signal via the M electrode, and the current signal is generated by the voltage and an impedance of a stratum corneum of the user's skin.

7. The apparatus of claim 4, wherein the measurement control module comprises:
   a signal converter to convert the current signal into a voltage signal;
   a high-pass filter to high-pass filter the voltage signal to generate an AC voltage signal;
   a signal supplier to generate an out-of-phase signal with respect to the voltage signal;
   a susceptance measurement unit measuring susceptance of the current signal by synchronizing the AC voltage signal and the out-of-phase signal received from the signal supplier;
   a low-pass filter to low-pass filter the voltage signal to generate a DC voltage signal; and
   a conductance measurement unit to measure conductance of the current signal from the DC voltage signal.

8. The apparatus of claim 7, wherein the measurement control module measures the sweat gland activity of the user's skin from the conductance of the current signal, and measures the skin moisture content of the user's skin from the susceptance of the current signal.

9. A method of measuring skin moisture content, the method comprising:
   generating an in-phase signal and an out-of-phase signal based on a voltage signal obtained from a user's skin, and supplying the generated in-phase signal and the out-of-phase signal to the voltage signal;
   measuring conductance of the voltage signal by synchronizing the voltage signal and the in-phase signal;

measuring susceptance of the voltage signal by synchronizing the voltage signal and the out-of-phase signal, wherein the conductance is measured at the same time as the susceptance; and simultaneously outputting sweat gland activity information of the user based on the measured conductance and skin moisture content information of the user based on the measured susceptance, thereby providing skin moisture content information that takes sweat gland activity into account.

10. The method of claim 9, further comprising supplying two power voltages to the user's skin, and detecting a current signal in the user's skin.

11. The method of claim 10, further comprising converting the current signal into a voltage signal.

12. The method of claim 9, wherein the sweat gland activity information and the skin moisture content information are output to a display.

13. A method of measuring skin moisture content, the method comprising:

supplying a single power voltage to the skin of a user, and detecting a current signal in the skin of the user;

converting the current signal into a voltage signal;

high-pass filtering the voltage signal to generate an AC voltage signal;

generating an out-of-phase signal with respect to the voltage signal to supply to the AC voltage signal;

measuring susceptance of the current signal by synchronizing the AC voltage signal and the out-of-phase signal;

low-pass filtering the voltage signal to generate a DC voltage signal; and measuring conductance of the current signal from the DC voltage signal.

14. At least one non-transitory medium comprising computer readable code to control at least one processing element to implement a method of measuring skin moisture content, the method comprising:

generating an in-phase signal and an out-of-phase signal based on a voltage signal obtained from a user's skin, and supplying the generated in-phase signal and the out-of-phase signal to the voltage signal;

measuring conductance of the voltage signal by synchronizing the voltage signal and the in-phase signal;

measuring susceptance of the voltage signal by synchronizing the voltage signal and the out-of-phase signal, wherein the conductance is measured at the same time as the susceptance; and simultaneously outputting sweat gland activity information of the user based on the measured conductance and skin moisture content information of the user based on the measured susceptance, thereby providing skin moisture content information that takes sweat gland activity into account.

15. An apparatus measuring skin moisture content in a user's skin, the apparatus comprising:

a signal supplier to generate an out-of-phase signal from a voltage signal obtained from the user's skin and an in-phase signal from the voltage signal;

a susceptance measurement unit to measure susceptance of the voltage signal by synchronizing the voltage signal and the out-of-phase signal received from the signal supplier;

a conductance measurement unit to measure conductance of the voltage signal by synchronizing the voltage signal and the in-phase signal, wherein the conductance measurement unit measures the conductance simultaneously with the susceptance measurement unit's measurement of the susceptance; and an output unit to simultaneously output sweat gland activity information of the user based on the measured conductance and skin moisture content information of the user based on the measured susceptance, thereby providing skin moisture content information that takes sweat gland activity into account.

* * * * *